(12) United States Patent
Zhang

(10) Patent No.: US 12,603,169 B2
(45) Date of Patent: Apr. 14, 2026

(54) INTELLIGENT TRIAGE METHOD AND DEVICE, STORAGE MEDIUM AND ELECTRONIC DEVICE

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 798 days.

(21) Appl. No.: 17/907,775

(22) PCT Filed: Jun. 30, 2021

(86) PCT No.: PCT/CN2021/103444
§ 371 (c)(1),
(2) Date: Aug. 29, 2022

(87) PCT Pub. No.: WO2023/272563
PCT Pub. Date: Jan. 5, 2023

(65) Prior Publication Data
US 2024/0203569 A1     Jun. 20, 2024

(51) Int. Cl.
*G16H 40/20* (2018.01)
*G06F 40/30* (2020.01)
(Continued)

(52) U.S. Cl.
CPC ............. *G16H 40/20* (2018.01); *G06F 40/30* (2020.01); *G06F 40/40* (2020.01); *G16H 50/20* (2018.01); *G06F 16/35* (2019.01)

(58) Field of Classification Search
CPC ........ G16H 40/20; G16H 50/20; G06F 40/30; G06F 40/40
See application file for complete search history.

(56) References Cited

U.S. PATENT DOCUMENTS 6,055,506 A * 4/2000 Frasca, Jr. .............. G16H 20/10
705/2
2011/0295620 A1* 12/2011 Loscalzo ................ G16H 10/20
705/3
(Continued)

FOREIGN PATENT DOCUMENTS

CN        108877946 A      11/2018
CN        109635122 A      4/2019
(Continued)

OTHER PUBLICATIONS

Saleem, et al. "Multi-objective long-short term memory recurrent neural networks for speech enhancement", Oct. 16, 2020, 16 pgs., Journal of Ambient Intelligence and Humanized Computing.

(Continued)

*Primary Examiner* — Kambiz Abdi
*Assistant Examiner* — Tran N Nguyen
(74) *Attorney, Agent, or Firm* — Calfee, Halter & Griswold LLP

(57)     ABSTRACT

The present disclosure provides an intelligent triage method and device, a storage medium and an electronic device. The method includes: obtaining disease information of a target outpatient, and obtaining a vector of the target outpatient according to the disease information; vectorizing each doctor in a doctor knowledge graph to obtain a plurality of doctor vectors; and calculating matching degrees between the vector of the target outpatient and the plurality of doctor vectors using a matching degree calculation model, and recommending a doctor for the target outpatient according to magnitudes of the matching degrees.

12 Claims, 4 Drawing Sheets

(51) Int. Cl.
    *G06F 40/40*     (2020.01)
    *G16H 50/20*     (2018.01)
    *G06F 16/35*     (2019.01)

(56)           References Cited

U.S. PATENT DOCUMENTS

| | | | |
|---|---|---|---|
| 2012/0089420 A1* | 4/2012 | Hoffman | G16H 50/20 |
| | | | 705/3 |
| 2012/0109683 A1* | 5/2012 | Ebadollahi | G16H 10/60 |
| | | | 705/3 |
| 2013/0197940 A1* | 8/2013 | Garber | G16H 10/60 |
| | | | 705/3 |
| 2017/0175169 A1* | 6/2017 | Lee | G01N 33/54373 |
| 2019/0006027 A1* | 1/2019 | Sacaleanu | G16H 50/30 |
| 2020/0020435 A1 | 1/2020 | Annavi | |
| 2021/0109995 A1 | 4/2021 | Mihindukulasooriya | |
| 2021/0279422 A1 | 9/2021 | Mihindukulasooriya | |

FOREIGN PATENT DOCUMENTS

| | | |
|---|---|---|
| CN | 110442732 A | 11/2019 |
| CN | 110675944 A | 1/2020 |
| CN | 110993078 A | 4/2020 |
| CN | 111785368 A | 10/2020 |
| CN | 112037912 A | 12/2020 |

OTHER PUBLICATIONS

"Bi-LSTM+GCN Causality Extraction Based on Time Relationship", Journal of Jilin University, vol. 59, No. 3, 6 pgs., May 2021.
Written Opinion from PCT/CN2021/103444 dated Mar. 28, 2022.
International Search Report from PCT/CN2021/103444 dated Mar. 28, 2022.

* cited by examiner

100

200

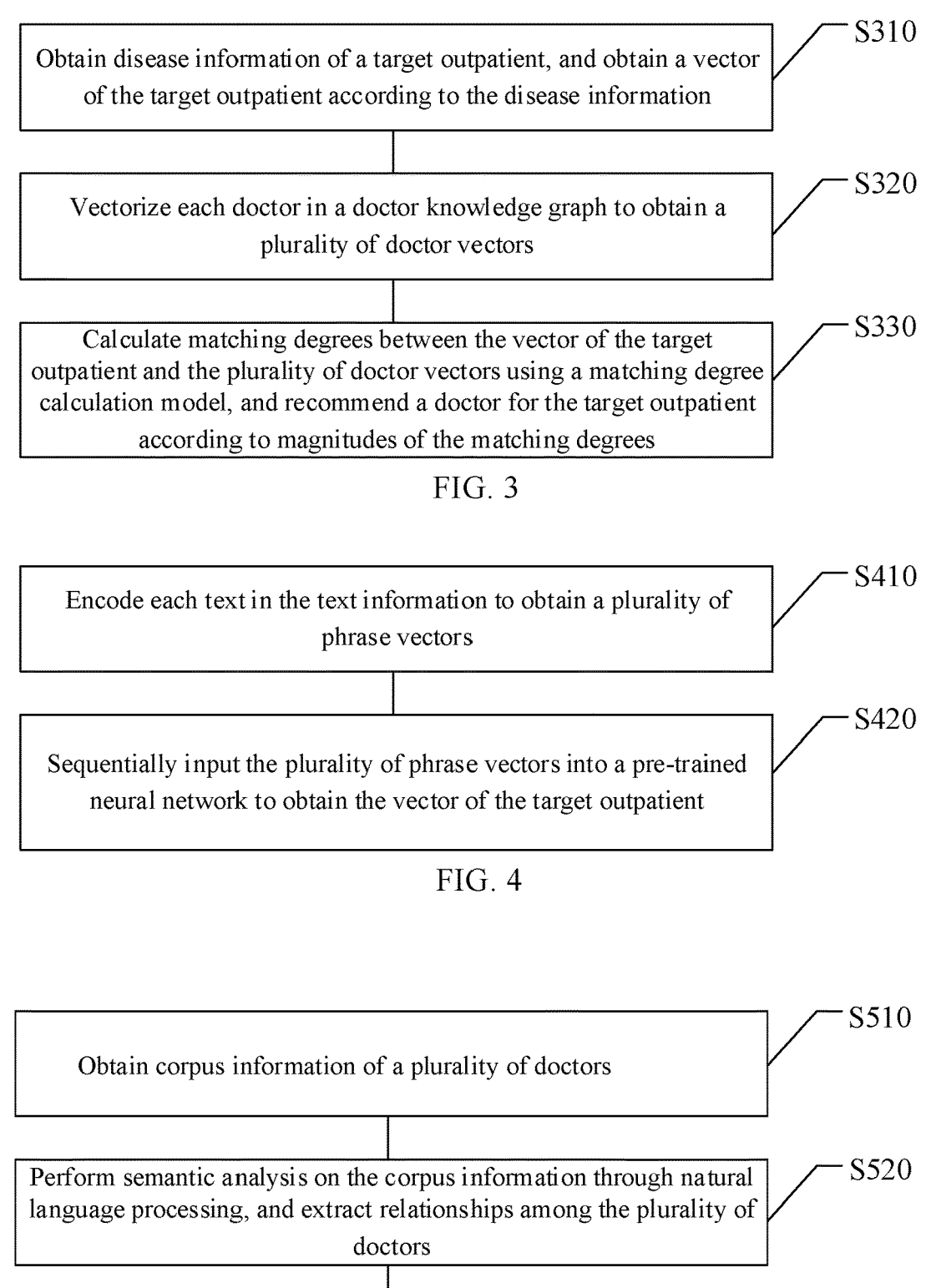

Obtain disease information of a target outpatient, and obtain a vector of the target outpatient according to the disease information ⟋ ⌐S310

Vectorize each doctor in a doctor knowledge graph to obtain a plurality of doctor vectors ⟋ ⌐S320

Calculate matching degrees between the vector of the target outpatient and the plurality of doctor vectors using a matching degree calculation model, and recommend a doctor for the target outpatient according to magnitudes of the matching degrees ⟋ ⌐S330

FIG. 3

Encode each text in the text information to obtain a plurality of phrase vectors ⟋ ⌐S410

Sequentially input the plurality of phrase vectors into a pre-trained neural network to obtain the vector of the target outpatient ⟋ ⌐S420

FIG. 4

Obtain corpus information of a plurality of doctors ⟋ ⌐S510

Perform semantic analysis on the corpus information through natural language processing, and extract relationships among the plurality of doctors ⟋ ⌐S520

With the plurality of doctors as entities, construct the doctor knowledge graph according to the relationships among the plurality of doctors ⟋ ⌐S530

Initialize node vectors corresponding to individual doctors in the doctor knowledge graph

S720

Iteratively update each of the node vectors by using a pre-trained graph neural network to obtain the plurality of doctor vectors

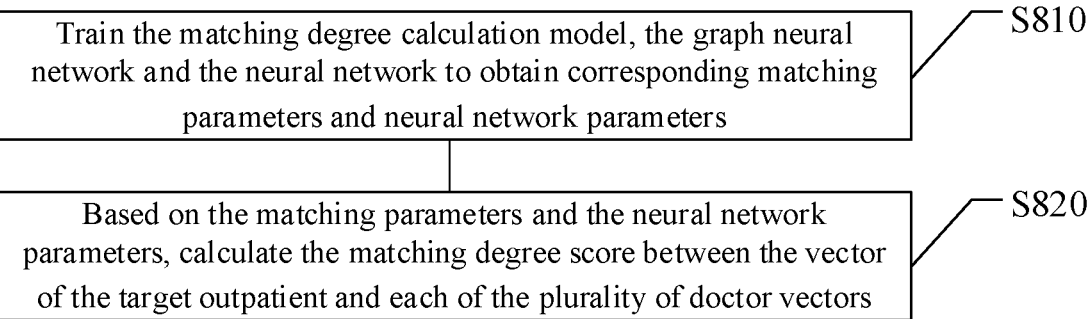

Train the matching degree calculation model, the graph neural network and the neural network to obtain corresponding matching parameters and neural network parameters ⌐ S810

Based on the matching parameters and the neural network parameters, calculate the matching degree score between the vector of the target outpatient and each of the plurality of doctor vectors ⌐ S820

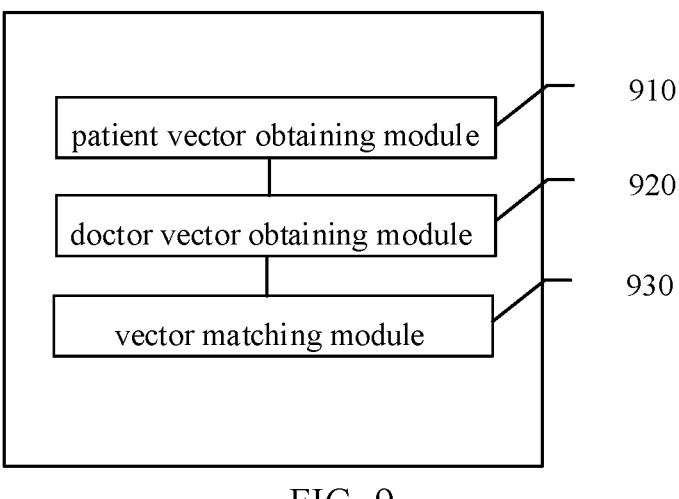

patient vector obtaining module ⌐ 910 doctor vector obtaining module ⌐ 920 vector matching module ⌐ 930

FIG. 9

INTELLIGENT TRIAGE METHOD AND DEVICE, STORAGE MEDIUM AND ELECTRONIC DEVICE

RELATED APPLICATIONS

This application is the national stage entry of PCT/CN2021/103444, filed on Jun. 30, 2021, titled INTELLIGENT TRIAGE METHOD AND DEVICE, STORAGE MEDIUM AND ELECTRONIC DEVICE, the entire disclosure of which is hereby incorporated by reference.

TECHNICAL FIELD

The present disclosure relates to the artificial intelligence technical field, and in particular, to an intelligent triage method, an intelligent triage device, a computer-readable storage medium and an electronic device.

BACKGROUND

With the development of Internet technologies, intelligent recommendation systems have been deeply embedded in people's lives. For example, an intelligent recommendation system can recommend meals, scenic spots, and transportation plans that meet users' needs for users to choose from.

At present, when using an intelligent recommendation system to recommend a consulting doctor for a patient, the intelligent recommendation system usually finds a doctor label with high degree of relevance in the intelligent recommendation system based on the patient's self-reported symptoms, and recommends a corresponding consulting doctor for the patient according to the retrieved doctor label.

It should be noted that the information in the background section above is only used to enhance the understanding of the background of the present disclosure, and therefore may include information that does not constitute the prior art known to those of ordinary skill in the art.

SUMMARY

Embodiments of the present disclosure provide an intelligent triage method, an intelligent triage device, a computer-readable storage medium and an electronic device.

An embodiment of the present disclosure provides an intelligent triage method, including:

obtaining disease information of a target outpatient, and obtaining a vector of the target outpatient according to the disease information;

vectorizing each doctor in a doctor knowledge graph to obtain a plurality of doctor vectors; and calculating matching degrees between the vector of the target outpatient and the plurality of doctor vectors using a matching degree calculation model, and recommending a doctor for the target outpatient according to magnitudes of the matching degrees.

In an example embodiment of the present disclosure, the disease information includes text information;

wherein obtaining the vector of the target outpatient according to the disease information includes:

encoding each text in the text information to obtain a plurality of phrase vectors; and sequentially inputting the plurality of phrase vectors into a pre-trained neural network to obtain the vector of the target outpatient.

In an example embodiment of the present disclosure, the method further includes:

obtaining corpus information of a plurality of doctors;

performing semantic analysis on the corpus information through natural language processing, and extracting relationships among the plurality of doctors; and with the plurality of doctors as entities, constructing the doctor knowledge graph according to the relationships among the plurality of doctors.

In an example embodiment of the present disclosure, vectorizing each doctor in the doctor knowledge graph to obtain the plurality of doctor vectors includes:

vectorizing each doctor in the doctor knowledge graph through a graph neural network to obtain the plurality of doctor vectors.

In an example embodiment of the present disclosure, vectorizing each doctor in the doctor knowledge graph through the graph neural network to obtain the plurality of doctor vectors includes:

initializing node vectors corresponding to individual doctors in the doctor knowledge graph; and iteratively updating each of the node vectors by using a pre-trained graph neural network to obtain the plurality of doctor vectors.

In an example embodiment of the present disclosure, iteratively updating each of the node vectors by using the pre-trained graph neural network to obtain the plurality of doctor vectors includes:

updating each of the node vectors according to the following equation to obtain the plurality of doctor vectors:

$$h^{t+1}(e_i) =$$

$$\sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

wherein $W_p$, $W_{ph}$, $W_c$, and $W_{ch}$ are parameters of the graph neural network, $\sigma$ is an activation function in the graph neural network, t is number of network iterations, $e_i$ is a node corresponding to an i-th doctor in the doctor knowledge graph, $Np(e_i)$ is a parent node set for the node $e_i$, $e_k$ is a k-th parent node of the node $e_i$, $Nc(e_i)$ is a child node set for the node $e_i$, $e_j$ a j-th child node of the node $e_i$, and $h^t (e_i)$ represents a vector of the node $e_i$ after t network iterations.

In an example embodiment of the present disclosure, calculating the matching degrees between the vector of the target outpatient and the plurality of doctor vectors using the matching degree calculation model includes:

calculating a matching degree score between the vector of the target outpatient and each of the plurality of doctors according to:

score(doc$_i$,pat$_j$)=v$^T$σ(W[doc$_i$,pat$_j$]+b);

wherein [doc$_i$,pat$_j$] is a vector obtained by concatenating a i-th doctor vector doc$_i$ and the vector pat$_j$ of the target outpatient, W, v and b are matching parameters, and σ is an activation function in the matching degree calculation model.

In an example embodiment of the present disclosure, the method further includes:

training the matching degree calculation model, the graph neural network and the neural network to obtain corresponding matching parameters and neural network parameters; and based on the matching parameters and the neural network parameters, calculating the matching degree score between the vector of the target outpatient and each of the plurality of doctor vectors.

In an example embodiment of the present disclosure, training the matching degree calculation model to obtain the matching parameters of the matching degree calculation model includes:

obtaining a training data set, wherein the training data set includes a positive training data set and a negative training data set;

inputting the training data set into the matching degree calculation model, and constructing an objective function; and determining the matching parameters of the matching degree calculation model according to the objective function.

In an example embodiment of the present disclosure, determining the matching parameters of the matching degree calculation model according to the objective function includes:

updating the matching parameters of the matching degree calculation model using a stochastic gradient descent algorithm, and when the objective function converges, completing the training of the matching parameters.

In an example embodiment of the present disclosure, the objective function is:

$$L = \sum_{(doc_i, pat_i)} \sum_{(doc_j, pat_i)} [\text{score}(doc_j, \ pat_i) + \gamma - \text{score}(doc_i, \ pat_i)]_+$$

wherein $(doc_i, pat_i)$ is positive training data and represents that an i-th doctor is suitable for dealing with a disease of an i-th patient, $(doc_j, pat_i)$ is negative training data and represents that a j-th doctor is not suitable for dealing with a disease of the i-th patient, $\gamma$ represents a preset difference threshold between a matching degree score $\text{score}(doc_i, pat_i)$ of the positive training data and a matching degree score $\text{score}(doc_j, pat_i)$ of the negative training data.

In an example embodiment of the present disclosure, training the graph neural network to obtain neural network parameters of the graph neural network includes:

iteratively updating the neural network parameters of the graph neural network by using a backpropagation algorithm, and when an objective function converges, completing the training of the neural network parameters.

In an example embodiment of the present disclosure, recommending the doctor for the target outpatient according to magnitudes of the matching degrees includes:

determining a set of doctors to be recommended according to the magnitudes of the matching degrees; and recommending the doctor for the target outpatient based on the set of doctors to be recommended.

In an example embodiment of the present disclosure, recommending the doctor for the target outpatient based on the set of doctors to be recommended includes:

recommending the set of doctors to be recommended to the target outpatient; and according to a filtering condition input by the target outpatient, performing filtering on each doctor in the set of doctors to be recommended, so as to recommend a target doctor for the target outpatient.

An embodiment of the present disclosure provides an intelligent triage device, including:

a patient vector obtaining module configured to obtain disease information of a target outpatient, and obtain a vector of the target outpatient according to the disease information;

a doctor vector obtaining module configured to vectorize each doctor in a doctor knowledge graph to obtain a plurality of doctor vectors; and a vector matching module configured to calculate matching degrees between the vector of the target outpatient and the plurality of doctor vectors using a matching degree calculation model, and recommend a doctor for the target outpatient according to magnitudes of the matching degrees.

An embodiment of the present disclosure provides a computer-readable storage medium having a computer program stored thereon. When the computer program is executed by a processor, the processor is caused to perform the method according to any one of the above embodiments.

An embodiment of the present disclosure provides an electronic device, including:

a processor; and a memory storing instructions executable by the processor;

wherein the processor is configured to perform the method of any of the above embodiments by executing the executable instructions.

It should be understood that the above general description and the following detailed description are only exemplary and explanatory, and should not be construed as constituting any limitation on the present disclosure.

BRIEF DESCRIPTION OF THE DRAWINGS

The drawings, which are incorporated into the specification and constitute a part of the specification, show embodiments that comply with the present disclosure, and are used to explain the principles of the disclosure together with the specification. Obviously, the drawings in the following description only show some embodiments of the present disclosure. For those of ordinary skill in the art, other drawings can be obtained based on these drawings without creative work.

FIG. 3 schematically shows a flowchart of an intelligent triage method according to an embodiment of the present disclosure.

FIG. 4 schematically shows a flowchart of obtaining a target outpatient vector according to an embodiment of the present disclosure.

FIG. 5 schematically shows a flowchart of constructing a doctor knowledge graph according to an embodiment of the present disclosure.

FIG. 8 schematically shows a flowchart of doctor-patient matching according to an embodiment of the present disclosure.

FIG. 9 schematically shows a block diagram of an intelligent triage device according to an embodiment of the present disclosure.

DETAILED DESCRIPTION

Figure 1:
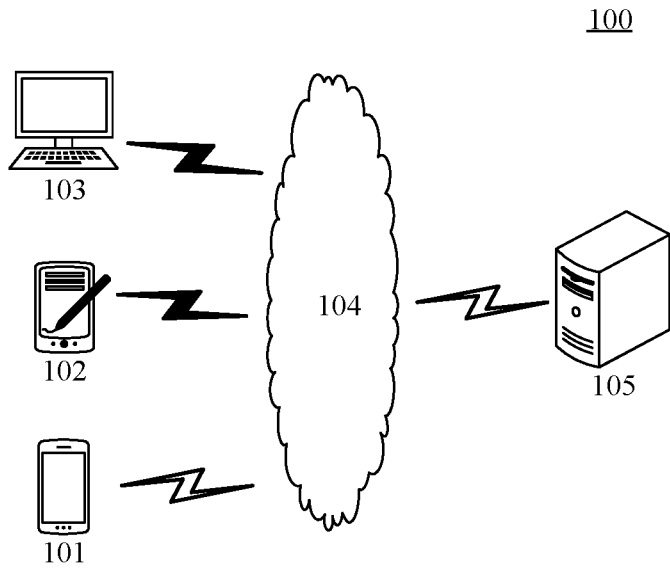
FIG. 1 shows a schematic diagram of an example system architecture in which an intelligent triage method and device according to embodiments of the present disclosure may be applied.

Example embodiments will now be described more fully with reference to the accompanying drawings. However, the embodiments can be implemented in a variety of forms and should not be construed as being limited to the examples set forth herein; rather, these embodiments are provided so that the present disclosure will be more complete so as to convey the idea of the example embodiments to those skilled in this art. The described features, structures, or characteristics may be combined in any suitable manner in one or more embodiments. In the following description, numerous specific details are provided in order to give a thorough understanding of the embodiments of the present disclosure. However, those skilled in the art will appreciate that the technical solutions of the present disclosure may be practiced without one or more of the specific details, or other methods, components, devices, steps, etc. may be employed. In other instances, well-known solutions are not shown or described in detail to avoid obscuring aspects of the present disclosure.

Furthermore, the drawings are merely schematic illustrations of the present disclosure and are not necessarily drawn to scale. The same reference numerals in the drawings denote the same or similar parts, and thus their repeated descriptions will be omitted. Some of the block diagrams shown in the figures are functional entities that do not necessarily correspond to physically or logically separate entities. These functional entities may be implemented in software, or in one or more hardware modules or integrated circuits, or in different networks and/or processor devices and/or microcontroller devices.

FIG. 1 shows a schematic diagram of a system architecture of an example application environment to which an intelligent triage method and device according to embodiments of the present disclosure may be applied.

As shown in FIG. 1, the system architecture 100 of the intelligent triage system may include one or more of terminal devices 101, 102 and 103, a network 104 and a server 105. The network 104 is a medium used to provide communication links between the terminal devices 101, 102 and 103 and the server 105. The network 104 may include various connection types, such as wired, wireless communication links, or fiber optic cables and so on. The terminal devices 101, 102 and 103 may be various electronic devices, including but not limited to desktop computers, portable computers, smart phones, or tablet computers. It should be understood that the numbers of terminal devices, networks and servers in FIG. 1 are merely illustrative. There can be any number of terminal devices, networks and servers according to implementation needs. For example, the server 105 may be a server cluster composed of multiple servers, or the like.

The intelligent triage method provided by the embodiments of the present disclosure is generally performed by the server 105, and accordingly the intelligent triage device is generally set in the server 105. The server may send matching results to a terminal device after matching a target outpatient to a plurality of consulting doctors who can provide suitable treatments, and the terminal device displays the matching results to the outpatient for the outpatient to choose. However, those skilled in the art can easily understand that the intelligent triage method provided by the embodiments of the present disclosure can also be executed by one or more of the terminal devices 101, 102 and 103, and correspondingly, the intelligent triage device may be set in the terminal devices 101, 102, and 103. For example, after the method is executed by a terminal device, the terminal device directly display the matching results on the display screen of the terminal device, or the terminal device may provide the matching results to the outpatient by means of voice broadcast, and embodiments of the present disclosure do not impose specific limitation on this.

Figure 2:
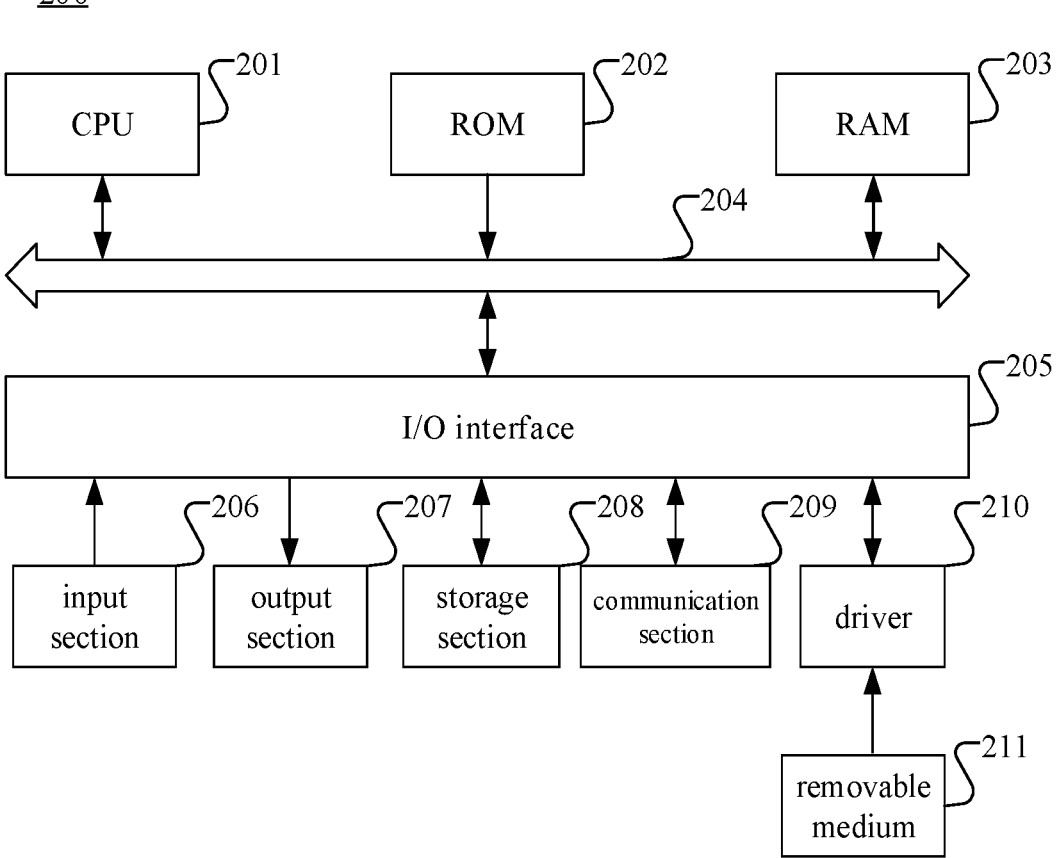
FIG. 2 shows a schematic structural diagram of a computer system suitable for implementing an electronic device according to an embodiment of the present disclosure.

FIG. 2 shows a schematic structural diagram of a computer system suitable for implementing an electronic device according to an embodiment of the present disclosure.

It should be noted that the computer system 200 of the electronic device shown in FIG. 2 is only an example, and should not impose any limitations on the functions and usage scope of the embodiments of the present disclosure.

As shown in FIG. 2, the computer system 200 includes a Central Processing Unit (CPU) 201 which performs various appropriate actions and processes according to a program stored in a Read Only Memory (ROM) 202 or according to a program which is loaded from a storage section 208 to a Random Access Memory (RAM) 203. The RAM 203 further stores various programs and data necessary for system operations. The CPU 201, the ROM 202 and the RAM 203 are connected to each other through a bus 204. An input/output (I/O) interface 205 is also connected to the bus 204.

The following components are connected to the I/O interface 205: an input section 206 including a keyboard, a mouse, etc.; an output section 207 including a cathode ray tube (CRT), a liquid crystal display (LCD), etc., and a speaker, etc.; the storage section 208 including a hard disk, etc.; and a communication section 209 including a network interface card such as a LAN card, a modem, and the like. The communication section 209 performs communication processing via a network such as the Internet. A driver 210 may also be connected to the I/O interface 205 as needed. A removable medium 211, such as a magnetic disk, an optical disk, a magnetic-optical disk, a semiconductor memory, etc., is mounted on the driver 210 as needed so that a computer program read therefrom is installed in the storage section 208 as needed.

In some embodiments, the intelligent triage methods described in embodiments of the present disclosure may be performed by a processor of an electronic device. In some embodiments, disease information of a target outpatient, corpus information of a plurality of doctors, and a training data set for constructing and training a matching degree calculation model may be input through the input section 206. For example, through a user interactive interface of the electronic device, the disease information of the target outpatient, the corpus information of the plurality of doctors and so on may be input. In some embodiments, matching degree scores between the target outpatient and the plurality of doctors may be output through the output section 207.

In particular, according to embodiments of the present disclosure, the processes described below with reference to the flowcharts may be implemented as computer software programs. For example, embodiments of the present disclosure include a computer program product including a computer program carried on a computer-readable medium. The computer program containing program codes for performing the methods illustrated in the flowcharts. In such embodiments, the computer program may be downloaded and installed from the network via the communication section 209 and/or installed from the removable medium 211. When the computer program is executed by the Central Processing Unit (CPU) 201, various functions defined in the methods and devices in embodiments of the present disclosure are performed.

As another aspect, an embodiment of the present application also provides a computer-readable medium. The computer-readable medium may be included in the electronic device described in the above embodiments; or, the computer-readable medium may exist alone without being assembled into the electronic device. The above-mentioned computer-readable medium carries one or more programs, and when the above-mentioned one or more programs are executed by an electronic device, the electronic device is caused to implement the methods described in the following embodiments. For example, the electronic device may implement the steps shown in FIG. 3 to FIG. 5, and FIG. 7 and FIG. 8.

It should be noted that the computer-readable medium shown in embodiments of the present disclosure may be a computer-readable signal medium or a computer-readable storage medium, or any combination of the two. The computer-readable storage medium may be, for example, but is not limited to, an electronic, magnetic, optical, electromagnetic, infrared, or semiconductor system, apparatus, or device, or any combination thereof. More specific examples of the computer-readable storage medium may include but is not limited to: electrical connection with one or more wires, portable computer magnetic disk, hard disk, random access memory (RAM), read-only memory (ROM), erasable programmable read-only memory (EPROM or flash memory), optical fiber, portable compact magnetic disc read-only memory (CD-ROM), optical storage device, magnetic storage device, or any suitable combination of the foregoing. In embodiments of the present disclosure, the computer-readable storage medium may be any tangible medium that contains or stores a program that may be used by or in conjunction with an instruction execution system, apparatus, or device. In embodiments of the present disclosure, the computer-readable signal medium may include a data signal in baseband or propagated as part of a carrier wave, which carries computer-readable program codes. Such a propagated data signal may have many forms, including but not limited to electromagnetic signals, optical signals, or any suitable combination of the foregoing. The computer-readable signal medium may also be any computer-readable medium other than a computer-readable storage medium, and the computer-readable medium may send, propagate, or transmit a program that is used by an instruction execution system, apparatus, or device, or that is used in combination with an instruction execution system, apparatus, or device. The program codes contained on the computer-readable medium may be transmitted using any appropriate medium, including but not limited to wireless, electric wired, optical fiber, RF, etc., or any suitable combination of the foregoing.

The technical solutions of the embodiments of the present disclosure will be described in detail below.

At present, when using an intelligent recommendation system to recommend a consulting doctor for a patient, the intelligent recommendation system usually finds a doctor label with high degree of relevance in the intelligent recommendation system based on the patient's self-reported symptoms, and recommends a corresponding consulting doctor for the patient according to the retrieved doctor label. However, when the doctor label stored in the intelligent recommendation system is inconsistent with the actual professional ability of the doctor, even if the consulting doctor selected by the intelligent recommendation system has a high matching degree with the patient, there may be a possibility that the recommended consulting doctor is not good at treating the patient's disease, which may bring poor patient experience.

Exemplarily, by adding or obscuring doctor labels, the probability of doctors being retrieved can be improved. However, adding or obscuring doctor labels may introduce noise and affect the accuracy of doctor-patient matching. For example, for a doctor specializing in endodontics, a label of the doctor in the database might be "specialized in oral diseases", and there may be a high degree of matching between the doctor and a patient who needs an impacted tooth extraction surgery (because the impacted tooth extraction is an oral disease). However, it can be seen that for a patient who need the impacted tooth extraction surgery, a doctor who is good at endodontic treatment is not a consulting doctor who can provide suitable treatments for the patient, and thus this may bring poor patient visiting experience during the patient's visit.

In view of one or more of the above-mentioned problems, an embodiment of the present disclosure provides an intelligent triage method, which may be applied to the above-mentioned server 105 or one or more of the above-mentioned terminal devices 101, 102 and 103. This is not particularly limited in the example embodiment. Referring to FIG. 3, the intelligent triage method may include the following steps S310 to S330:

In step S310, disease information of a target outpatient is obtained, and a vector of the target outpatient is obtained according to the disease information.

In step S320, each doctor in a doctor knowledge graph is vectorized to obtain a plurality of doctor vectors.

In step S330, matching degrees between the vector of the target outpatient and the plurality of doctor vectors are calculated using a matching degree calculation model, and a doctor is recommended for the target outpatient according to magnitudes of the matching degrees.

In the intelligent triage method provided by the example embodiment of the present disclosure, the disease information of the target outpatient is obtained, and the vector of the target outpatient is obtained according to the disease information. Each doctor in the doctor knowledge graph is vectorized to obtain a plurality of doctor vectors. Matching degrees between the vector of the target outpatient and the plurality of doctor vectors are calculated using the matching degree calculation model, and a doctor is recommended for the target outpatient according to magnitudes of the matching degrees. The method maps the doctors to be recommended in the doctor knowledge graph into vectors, and performing doctor-patient matching in the corresponding vector space. Thus, the method can recommend more proper consulting doctors who can provide suitable treatments for the patient, thereby improving the patient's experience of seeing a doctor.

Hereinafter, the above steps of the example embodiment will be described in more detail.

In step S310, disease information of the target outpatient is obtained, and the vector of the target outpatient is obtained according to the disease information.

In this example embodiment, the target outpatient may be a patient who needs to be triaged before an emergency, or a patient who needs to be triaged in a normal clinic. For example, for a patient who needs to be triaged before the emergency, hospital staff can use the intelligent triage system to quickly triage the patient, so as to arrange the patient to see a doctor as soon as possible. For a patient who needs to be triaged in a normal clinic, the hospital staff can use the intelligent triage system to triage the patient, or the patient can use the intelligent triage system to triage, which is not specifically limited in this example. In other examples, the patient can also use the intelligent triage system to determine, before seeking medical treatment, a target hospital and a consulting doctor who can provide suitable treatments for the patient.

When the intelligent triage system is used for triage, the disease information of the target outpatient may be obtained. The disease information of the target outpatient may include basic information of the patient such as name, age and so on. The disease information may further include the patient's self-reported disease symptoms such as cough, fever and so on. The disease information may further include the patient's past medical records such as medical history, medication and so on, which is not specifically limited in this example. Exemplarily, the hospital staff may input the disease information of the target outpatient into the intelligent triage system, or the target outpatient may input his/her own disease information into the intelligent triage system by himself/herself. The hospital staff or the target outpatient may input the disease information manually, or input the disease information by voice, which is not specifically limited in this example.

After obtaining the disease information of the target outpatient, the patient may be vectorized according to the patient's disease information to obtain a vector representation of the patient, so as to match the patient vector with doctor vectors to determine a consulting doctor who can provide suitable treatments for the patient. Referring to FIG. 4, the vector representation of the target outpatient for consultation may be obtained according to steps S410 and S420.

In step S410, each text in the text information is encoded to obtain a plurality of phrase vectors.

Taking the target outpatient for triage by using the intelligent triage system by himself as an example, the patient's disease information may include text information, voice information, and may also include image and video information. In one example, the patient may input information such as his basic information, self-reported symptoms, and past medical records into the intelligent triage system by voice. The intelligent triage system may map the received voice information into corresponding text information, such as "Zhang San, 20-years old, toothache for three days". In other examples, the patient may also manually input his basic information, self-reported symptoms, past medical records and so on into the intelligent triage system, and the intelligent triage system may directly obtain the patient's text information.

After obtaining the text information of the target outpatient, such as "Zhang San, 20-years old, toothache for three days", the text information of the patient may be encoded. For example, each text in "Zhang San, 20-years old, toothache for three days" may be encoded by Embedding (vector mapping), and each word may be represented by a low-dimensional vector, and multiple corresponding word vectors may be obtained. For example, the vector representation of "Zhang" is obtained. It is also possible to use the phrase as a unit to encode each word contained in the phrase to obtain multiple corresponding phrase vectors, such as the vector representation of "Zhang San" may be obtained. Exemplarily, One-Hot encoding may be performed on each word. One-Hot encoding is also known as one-bit valid encoding. The method uses an N-bit state register to encode N states, and each state has an independent register bit. Only one bit in the register is valid at any time. It should be noted that the vector dimension of the One-Hot encoding will increase with the increase of the number of texts in the patient's text disease information, which may increase the computational complexity. In other examples, each word may be represented by a dense vector. For example, the Word2vec algorithm may be used to map each word in the acquired text disease information into a vector space, and each word may be represented by a word vector in the vector space. Similarly, Doc2vec algorithm, Glove algorithm, etc. may also be used to convert text into vectors.

In step S420, the plurality of phrase vectors are sequentially inputting into a pre-trained neural network to obtain the vector of the target outpatient.

It can be understood that symptoms in the text disease information of the outpatient are related. Therefore, in this example, the word vectors corresponding to all the words in the text disease information may be regarded as a time series, and then a neural network (for example, a recurrent neural network) performs operation on the word vector corresponding to each word. Exemplarily, after obtaining the word vector corresponding to each word in "Zhang San, 20-years old, toothache for three days", the eight word vectors may be input into a trained LSTM (Long Short-Term Memory) network in turn to obtain the vector representation of the patient "Zhang San". The LSTM network is a time-recurrent neural network suitable for processing and predicting important events with relatively long intervals and delays in time series.

Specifically, "word vector 1" corresponding to "Zhang" may be input into the LSTM network first, and the LSTM network extracts a hidden feature for "word vector 1" and outputs a hidden vector at this time, such as at time t. Then, the hidden vector at time t and the "word vector 2" corresponding to "San" at time t+1 may be concatenated. The concatenated vector may be input into the LSTM network, and hidden feature extraction may be performed for the concatenated vector to output the hidden vector at time t+1. Similarly, the word vector at the current time may be concatenated with the hidden vector passed down at the previous time in turn, and feature extraction may be performed by the LSTM network for the concatenated vector, until the "word vector 8" corresponding to "days" is finally input into the LSTM network. The hidden vector outputted at the last time is used to represent all words, and the hidden vector is the vector representation of the patient "Zhang San", for example, it may be recorded as $pat_j$. In other examples, the GRU (Gated Recurrent Unit) network may also be used to perform operations on the word vector corresponding to each word. The structure of the GRU network is simpler than that of the LSTM network, and the implementation effect is the same as that of the LSTM network.

It should be noted that, in order to perform doctor-patient matching in the embodiments of the present disclosure, that is, to calculate the matching degree between a patient vector and a doctor vectors, it may be preferable that the vector dimension of the patient vector may be the same as the vector dimension of the doctor vector. For example, both doctor and patient may be mapped as a 256-dimensional vector. It can be understood that the number of vector dimensions of the doctor vector and the patient vector is only illustrative, and in other examples, both the doctor and the patient may be mapped as a 128-dimensional vector, which is not specifically limited in the present disclosure.

In step S320, each doctor in the doctor knowledge graph is vectorized to obtain a plurality of doctor vectors.

In order to avoid the inconsistency between a doctor label stored in the intelligent recommendation system and the doctor's actual professional ability, relationships between doctors may be used for modeling. Exemplarily, a doctor knowledge graph may be constructed by using multiple doctors and relationships among multiple doctors. By mapping the doctor(s) to be recommended in the doctor knowledge graph into vector(s), and performing doctor-patient matching in a corresponding vector space, a consulting doctor who can provide suitable treatments for the patient can be recommended to the patient, which can improve patient visiting experience.

The knowledge graph is a graph-based data structure, which may be composed of nodes and edges. In a knowledge graph, nodes may represent entities or concepts, and edges may be composed of attributes or relationships. A knowledge graph is a relational network that may connect different kinds of information together, and it is a way to effectively represent relationships. Therefore, the knowledge graph may be used to analyze the problem from the perspective of "relationship". Correspondingly, in this example, the doctor knowledge graph may be a knowledge graph including multiple doctors (nodes) and relationships (edges) between multiple doctors. Referring to FIG. 5, a doctor knowledge graph may be constructed according to steps S510 to S530.

In step S510, corpus information of a plurality of doctors is obtained.

In an example implementation, a crawler may be used to crawl corpus information of multiple doctors from the Internet. For example, the corpus information may include information such as doctors' name, age, graduate school, work place, field of expertise, published articles, etc., and embodiments do not impose specific limitation on this. Exemplarily, a web crawler may be used to realize the mining of doctor information. A web crawler refers to writing a crawler script to obtain doctor information. The basic workflow may include the following. First, some URLs (Uniform Resource Locator) may be selected as seeds. The URLs are put into a queue to be crawled. Then, a crawler script is written. For the seed URLs in the queue to be crawled, the website may be accessed by simulating manual browsing. The crawled web HTML (Hyper Text Markup Language) data including doctor information is stored and parsed, and a new link obtained by parsing may be used as the seed URL for next layer crawling. In this example, the script tool can quickly and conveniently obtain the corpus information of multiple doctors. In other embodiments, the corpus information of multiple doctors may also be directly obtained by manual input or copy input.

In step S520, semantic analysis is performed on the corpus information through natural language processing, and relationships among the plurality of doctors are extracted.

After obtaining the corpus information of multiple doctors, natural language processing may be used to perform semantic analysis on the corpus information of the multiple doctors, and the relationships among the multiple doctors may be extracted. Natural language processing means that a computer may accept input in the form of a user's natural language, and internally perform a series of operations such as processing and calculation through algorithms defined by humans to simulate human understanding of natural language and return the results expected by users. Exemplarily, unsupervised learning may be used to perform clustering to achieve relationship extraction. Semi-supervised learning may also be used to achieve relationship extraction. For example, a part of corpus information may be selected for annotation, and the annotated corpus information may be iterated. It is also possible to use supervised learning for classification and a large number of annotations to achieve relationship extraction, or to extract relationships by training an end-to-end annotation model based on deep learning end-to-end joint annotation.

In one example, five relationships among multiple doctors may be extracted, which may be teacher-student relationship, sharing-of-same-tutor relationship, colleague relationship, alumni relationship, and collaborator relationship. For example, for doctor A and doctor B, when the two have the same teacher or the same colleague, it may indicate that the diseases they are good at treating may be similar. Exemplarily, doctor A is good at treating dental pulp diseases, and his students, senior apprentice or colleagues are more likely to be good at treating dental pulp diseases.

In step S530, with the plurality of doctors as entities, the doctor knowledge graph is constructed according to the relationships among the plurality of doctors.

Figure 6:
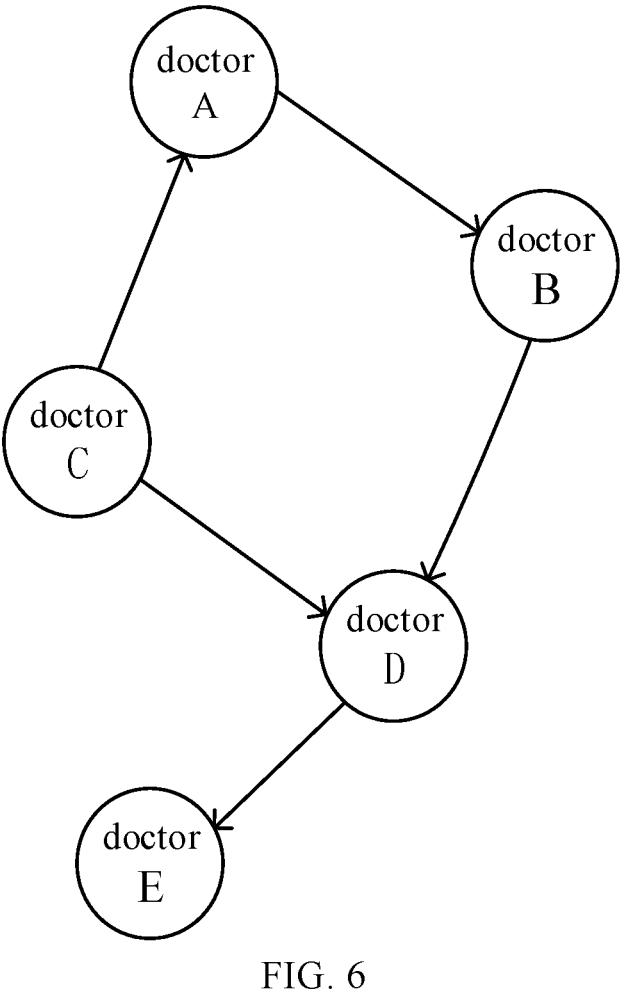
FIG. 6 schematically shows a schematic diagram of a doctor knowledge graph according to an embodiment of the present disclosure.
Figure 7:
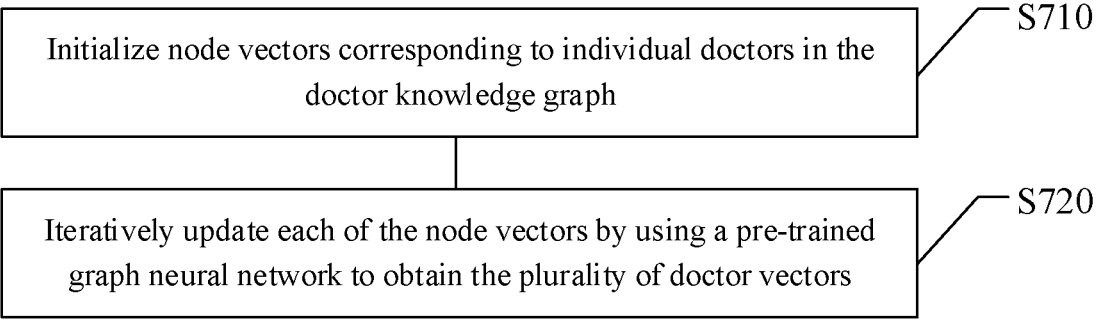
FIG. 7 schematically shows a flowchart of obtaining a doctor vector according to an embodiment of the present disclosure.

In this example, a doctor knowledge graph may be constructed. The entities of the doctor knowledge graph may be various doctors, and the relationships between the entities may include multiple relationships, for example, five kinds of relationships, namely, teacher-student relationship, sharing-of-same-tutor relationship, colleague relationship, alumni relationship, and collaborator relationship. Referring to FIG. 6, in order to more intuitively represent the relationships between various doctors, a doctor knowledge graph of a directed graph model may be constructed. The entities corresponding to the five nodes in the doctor knowledge graph are doctor A, doctor B, doctor C, doctor D and doctor E, respectively. For the node doctor A, the associated edges include an outgoing edge and an incoming edge. The node doctor A may be associated with the node doctor B through the outgoing edge, and the node doctor A may be associated with the node doctor C through the incoming edge. In this example, the node doctor C may be called as a parent node of the node doctor A, for example, the doctor C may be the teacher of the doctor A. The node doctor B may be called as a child node of the node doctor A. Similarly, it can be seen that node doctor D may be the child node of node doctor B and node doctor C at the same time, and node doctor D may also be the parent node of node doctor E.

The constructed doctor knowledge graph may be stored for subsequent access and invoking. Therefore, the doctor knowledge graph may be constructed in real time each time an intelligent triage is performed, or the doctor knowledge graph may be pre-built and stored in the database, for example, the doctor knowledge graph may be stored in Neo4j database (a high-performance NoSQL graph database). The doctor knowledge graph may be called or invoked when recommending to the patient a consulting doctor who can provide suitable treatments for the patient.

In an example implementation, the doctors to be recommended in the doctor knowledge graph may be mapped into vectors, so as to facilitate doctor-patient matching in a corresponding vector space. Exemplarily, each doctor in the doctor knowledge graph may be vectorized through a Graph Neural Network (GNN) to obtain multiple doctor vectors. The graph neural network may combine the doctor knowledge graph with the neural network, and perform end-to-end calculation on the doctor knowledge graph. The entire calculation process may be carried out along the structure of the doctor knowledge graph, which can not only retain the structure of the doctor knowledge graph, but also learn the structural information of the doctor knowledge graph. For example, a function map may be learned. By mapping a node e; in the doctor knowledge graph, the features of node $e_i$ may be aggregated with the features of neighbor node $e_j$ (such as parent node) and $e_k$ (such as child node) to generate a new representation of node $e_i$, that is, the hidden state $h(e_i)$ of each node may be obtained. It may be seen that for each node's hidden state, information from neighbor nodes may be included.

Illustratively, the graph neural network may generate a new representation of node $e_i$ by iteratively updating the hidden states of all nodes. Specifically, referring to FIG. 7, a graph neural network may be used to obtain representations of multiple nodes according to steps S710 and S720, that is, multiple doctor vectors may be obtained.

In step S710, node vectors corresponding to individual doctors in the doctor knowledge graph are initialized.

For example, the doctor knowledge graph may include N doctor nodes $\{e_i, i=1, \ldots, N\}$, and M edges $\{r_j, j=1, \ldots, M\}$. In this example, M=5 is used as an example for illustration. It can be understood that, according to the implementation requirements, the value of M may be arbitrary. The parameters in the graph neural network and the node vector corresponding to each doctor in the doctor knowledge graph may be randomly initialized to obtain the initial vectors of the nodes as follows: $h^0(e_i)$, $i=1, \ldots, N$.

In step S720, each of the node vectors is iteratively updated by using a pre-trained graph neural network to obtain the plurality of doctor vectors.

In an example, each of the node vectors may be updated according to the following equation to obtain the plurality of doctor vectors:

$$h^{t+1}(e_i) = \sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

where $W_p$, $W_{ph}$, $W_c$, and $W_{ch}$ are parameters of the graph neural network, $\sigma$ is an activation function in the graph neural network, for example the activation function may be Leaky ReLU (Leaky Rectified Linear Unit), t is number of network iterations, $e_i$ is the node corresponding to an i-th doctor in the doctor knowledge graph, $Np(e_i)$ is a parent node set for the node et, correspondingly $e_k$ is a k-th parent node of the node $e_i$, $Nc(e_i)$ is a child node set for the node $e_i$, correspondingly $e_j$ is a j-th child node of the node $e_i$, and $h^t(e_i)$ represents a vector representation of the node $e_i$ after t network iterations, which may be denoted as $doc_i$. The vector dimension may be the same as the vector dimension of the patient vector, e.g., the vector dimension may be 256 dimensions. Exemplarily, the preset number t of iterations may be 20, that is, the graph neural network may obtain the final vector representation of each node after 20 iterations.

In step S330, matching degrees between the vector of the target outpatient and the plurality of doctor vectors are calculated using a matching degree calculation model, and a doctor is recommended for the target outpatient according to magnitudes of the matching degrees.

In one example, after obtaining the disease information of the target outpatient, the vector representation corresponding to the patient may be obtained through the trained LSTM network, and then the matching degree between the patient and each doctor may be calculated through the trained matching degree calculation model, and ranking may be performed according to the magnitudes of the matching degrees.

Specifically, in the matching degree calculation model, a matching degree score between the vector $pat_j$ of the target outpatient and a doctor vector $doc_i$ may be calculated according to:

$$score(doc_i, pat_j) = v^T \sigma(W[doc_i, pat_j] + b)$$

where $[doc_i, pat_j]$ is a vector obtained by concatenating a i-th doctor vector $doc_i$ and the vector $pat_j$ of the target outpatient, W, v and b are matching parameters of the matching degree calculation model. For example, W may be a 256*512 parameter matrix, and v and b may be 256-dimensional column vectors or 256-dimensional row vectors. It should be noted that when v and b are both row vectors or column vectors, v and b may be transposed. When v and b are not both row vectors or column vectors, transposition is not necessary. The $\sigma$ is the activation function in the matching degree calculation model, such as Leaky ReLU (Leaky Rectified Linear Unit). Exemplarily, the matching degree score interval may be [0, 100], and the larger the matching degree score, the better the doctor may be in handling the patient's disease.

In another example, the matching degree calculation model, the graph neural network and the LSTM network may be pre-trained. After the training is completed, the vector representation corresponding to each doctor and the vector representation of the target outpatient may be obtained, and the vector corresponding to each doctor is stored in the database. For example, the vectors may be stored in a Redis database or in a MySQL database, which may be queried in real-time to get each doctor and the corresponding vector representation. Redis is a key-value storage system. When the vectors are stored in the Redis database, the following may be included: a key-value pair formed by a doctor's identity and a corresponding vector representation, where the key is the doctor's identity, and the value is the corresponding vector representation. As an efficient caching technology, Redis can support more than 100K+ read and write frequencies per second, and has certain advantages in data reading and storage speed. MySQL is an associative database management system. Associative database stores data in different tables instead of storing all data uniformly, increases storage speed and improves flexibility. MySQL has stable advantages in data storage and can avoid occurrence of data loss.

Exemplarily, as shown in FIG. 8, the matching degree calculation model, the graph neural network and the LSTM network are trained according to steps S810 and S820 to obtain the corresponding matching parameters and neural network parameters, so as to use the trained matching degree calculation model to perform doctor-patient matching.

In step S810, the matching degree calculation model, the graph neural network and the neural network are trained to obtain corresponding matching parameters and neural network parameters.

When training the matching degree calculation model, a training data set may be obtained. The training data set may include a positive training data set and a negative training data set. The positive training data set may be: $\{(doc_i, pat_j)\}$, $i=1, \ldots, K$, indicating that the i-th doctor is suitable for dealing with the disease of the i-th patient, that is, the i-th doctor is the consulting doctor who can provide suitable treatments for the i-th patient. The negative training data set may be: $\{(doc_j, pat_i)\}$, which means that the j-th doctor is not suitable for dealing with the disease of the i-th patient, that is, the j-th doctor is not a consulting doctor who can provide suitable treatments for the i-th patient. In one example, the negative training data set {(doc_j, pat_i)} may be obtained by randomly replacing the i-th doctor vector doc_i in (doc_i,pat_i) with other doctor vector doc_j(j≠i). Exemplarily, for each positive training data (doc_i,pat_i), 5 pieces of negative training data (doc_j, pat_i) may be generated by the random replacement method. It can be understood that the number of pieces of negative training data generated by random replacement for each positive training data is only illustrative, and any number of pieces of negative training data may be obtained, and combined with the positive training data, the matching degree calculation model may be trained multiple times to improve the performance of the matching degree calculation model.

After the training data set is obtained, the training data set may be input into the matching degree calculation model for training. In the training process, an objective function needs to be constructed first, so as to determine the matching parameters of the matching degree calculation model according to the objective function. The matching parameters may be parameters used to define the mapping relationships between the doctor vectors and the patient vector in the matching degree calculation model. The objective function, also known as the loss function, is the performance function in the matching degree calculation model, which may be used to estimate the inconsistency between the predicted value of the model and the true value.

In an example, the matching degree calculation model may be trained with the objective that the matching degree score between the patient pat; and the consulting doctor doc_i who can provide suitable treatments is the highest, this matching degree score is higher than the matching degree score between the patent pat; and other doctor doc_j by at least γ, and γ>0. Exemplarily, when γ=1, that is, score(doc_i, pat_i)>score(doc_j, pat_i)+1, where i, j∈[1, K], i≠j.

The corresponding objective function may be:

$$L = \sum_{(doc_i,pat_i)} \sum_{(doc_j,pat_i)} [score(doc_j, pat_i) + \gamma - score(doc_i, pat_i)]_+$$

where (doc_i,pat_i) is positive training data, (doc_j, pat_i) is negative training data, γ represents a preset difference threshold between a matching degree score score(doc_i, pat_i) of the positive training data and a matching degree score score(doc_j, pat_i) of the negative training data. When score(doc_j, pat_i)+γ−score(doc_i, pat_i)≤0, it means that the difference between the matching degree scores of the training data (doc_j, pat_i) and the training data (doc_i,pat_i) meets the requirement of being higher by at least γ, and it indicates that the matching degree calculation model in this case has no loss. When score (doc_j, pat_i)+γ−score(doc_i,pat_i)>0, it means that the difference between the matching degree scores of the training data (doc_j, pat_i) and the training data (doc_i,pat_i) does not meet the requirement of being higher by at least γ, and it indicates that the matching degree calculation model in this case has loss. The higher the value of score(doc_j, pat_i)+γ−score(doc_i,pat_i), the higher the corresponding loss. Thus, when [score(doc_j, pat_i)+ γ−score(doc_i,pat_i)]_+=0, the objective function may converge to a minimum value.

Exemplarily, a stochastic gradient descent algorithm may be used to update the matching parameters of the matching degree calculation model. According to the principle of backpropagation, the objective function is continuously calculated, and the parameters of the matching degree calculation model are updated according to the objective function. When the objective function converges to the minimum value, the training of the model parameters is completed, and the corresponding matching degree calculation model parameters at this time are the matching parameters. In other examples, the objective function may also be minimized by alternating least squares method, Adam optimization algorithm, etc., and the matching parameters are sequentially updated from the back to the front to optimize the matching parameters.

Exemplarily, the training process of the graph neural network may reverse iteratively update network parameters according to:

$$h^{t+1}(e_i) = \sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

When the preset number of iterations is satisfied, the training of the neural network parameters is completed, and the final doctor vector corresponding to each node may be obtained. Exemplarily, the preset number t of iterations may be 20, and the graph neural network is constantly updating network parameters in the process of performing 20 reverse iterations. After the iterations are completed, the final network parameters and the final vector representation of each node may be obtained. In other examples, the training parameters may also be determined according to the objective function L. For example, when the objective function L converges to the minimum value, the network parameters in the graph neural network may be obtained, and the final vector representation of each node may be determined according to the network parameters.

In an example, the training process of the LSTM network may use the backpropagation algorithm. By random initialization parameters, the parameters are updated continuously as the training deepens. For example, the BP (error Back Propagation) algorithm may be used. Specifically, the output of the output layer may be obtained by calculating from front to back according to the original input, and the objective function L may be calculated by calculating the difference between the current output and the target output. When the objective function L converges to the minimum, the parameters in the LSTM network may be obtained to determine the final vector representation of the target outpatient according to the parameters. In other examples, the gradient descent algorithm, Adam optimization algorithm, etc. may also be used to minimize the objective function L, and the parameters in the LSTM network may be updated sequentially from back to front.

In step S820, based on the matching parameters and the neural network parameters, the matching score between the target outpatient vector and each doctor vector is calculated.

After obtaining the neural network parameters, the target outpatient vector and each doctor vector may be correspondingly obtained. The matching degree score between the target outpatient vector and each doctor vector may be calculated according to the matching degree calculation model by using the matching parameters, the target outpatient vector and each doctor vector.

In the above training procedure, the parameters in the matching degree calculation model, the LSTM network and the graph neural network may be trained simultaneously. For example, with L as the objective function, parameters in the matching degree calculation model may be adjusted first. Since the doctor vectors and the target outpatient vector need to be used in the calculation process of the matching degree calculation model, they are further back-propagated to the LSTM network and graph neural network to adjust parameters in the LSTM network and the graph neural network. Through multiple layer-by-layer backpropagation, each model parameter may eventually converge, or the training may be terminated after a certain number of iterations. Through this training method, three models, i.e., the matching degree calculation model, the LSTM network and the graph neural network may be trained at the same time, ensuring higher precision and accuracy of each model, and improving training efficiency.

In one example, after obtaining the matching scores of the target outpatient and multiple doctors, the matching scores may be ranked, such as in a descending order. The top-ranked doctors may be formed into a set of doctors to be recommended, for example, the set of doctors to be recommended may be obtained from the top five doctors. Doctors whose matching degree scores are greater than a preset matching degree threshold may also be selected to obtain a set of doctors to be recommended. For example, when the matching score between the target outpatient and a doctor is greater than 80 points, the doctor may be regarded as the doctor to be recommended and added to the set of doctors to be recommended.

In this example, the set of doctors to be recommended may be recommended to the target outpatient. For example, the information of each doctor in the set of doctors to be recommended may be output to the terminal device, so that the outpatient may select the target consulting doctor from the set of doctors to be recommended. After receiving the information of each doctor in the set of doctors to be recommended, the outpatient may input a specific filter condition according to his/her own needs to perform secondary filtering on doctors in the set of doctors to be recommended. Exemplarily, when the patient selects a hospital within a certain distance to see a doctor, the doctors that exceed the distance required by the patient in the set of doctors to be recommended may be filtered out. Similarly, when the patient chooses a certain amount of medical treatment fee, doctors in the set of doctors to be recommended may also be filtered according to the fee, and the final consulting doctor may be recommended for the outpatient.

In this method, the doctors in the doctor knowledge graph may be mapped to vectors of a specified dimension through a graph neural network, and the patient's disease information may be mapped to a vector of the same dimension through a long short-term memory network, and matching degrees between the doctors and the patient in the vector space are calculated, so as to recommend a consulting doctor who can provide suitable treatments for the patient. This method can avoid the inconsistency between the doctor's label stored in the database and the doctor's actual professional ability, and improve the accuracy of doctor-patient matching.

In the intelligent triage method provided by the example embodiments of the present disclosure, disease information of a target outpatient is obtained, and a vector of the target outpatient is obtained according to the disease information. Each doctor in a doctor knowledge graph is vectorized to obtain a plurality of doctor vectors. Matching degrees between the vector of the target outpatient and the plurality of doctor vectors are calculated using a matching degree calculation model, and a doctor is recommended for the target outpatient according to magnitudes of the matching degrees. By mapping the doctors to be recommended in the doctor knowledge graph into vectors, and performing doctor-patient matching in a corresponding vector space, the methods in the present disclosure can recommend more proper consulting doctors who can provide suitable treatments for the patient, thereby improving the patient's experience of seeing a doctor.

It should be noted that although the various steps of the methods in embodiments of the present disclosure are depicted in the figures in a particular order, this does not require or imply that the steps must be performed in that particular order, or that all illustrated steps must be performed to achieve the desired result. Additionally or alternatively, certain steps may be omitted, multiple steps may be combined into one step, and/or one step may be decomposed into multiple steps, and the like.

An example embodiment of the present disclosure further provides an intelligent triage device. The device may be applied to a server or terminal device. Referring to FIG. 9, the intelligent triage device 900 may include a patient vector obtaining module 910, a doctor vector obtaining module 920, and a vector matching module 930.

The patient vector obtaining module 910 is configured to obtain disease information of a target outpatient, and obtain a vector of the target outpatient according to the disease information.

The doctor vector obtaining module 920 is configured to vectorize each doctor in a doctor knowledge graph to obtain a plurality of doctor vectors.

The vector matching module 930 is configured to calculate matching degrees between the vector of the target outpatient and the plurality of doctor vectors using a matching degree calculation model, and recommend a doctor for the target outpatient according to magnitudes of the matching degrees.

In an example implementation, the disease information includes text information;

the patient vector obtaining module 910 includes:

an information encoding module configured to encode each text in the text information to obtain a plurality of phrase vectors; and a patient vector determination module configured to sequentially input the plurality of phrase vectors into a pre-trained neural network to obtain the vector of the target outpatient.

In an example implementation, the device 900 further includes:

a corpus information obtaining module configured to obtain corpus information of a plurality of doctors;

a doctor relationship extraction module configured to perform semantic analysis on the corpus information through natural language processing, and extract relationships among the plurality of doctors; and a doctor knowledge graph construction module configured to, with the plurality of doctors as entities, construct the doctor knowledge graph according to the relationships among the plurality of doctors.

In an example implementation, the doctor vector obtaining module 920 includes:

A doctor vector obtaining sub-module configured o vectorize each doctor in the doctor knowledge graph through a graph neural network to obtain the plurality of doctor vectors.

In an example implementation, the doctor vector obtaining sub-module includes:

a vector initialization unit configured to initialize node vectors corresponding to individual doctors in the doctor knowledge graph; and a doctor vector obtaining unit configured to iteratively update each of the node vectors by using a pre-trained graph neural network to obtain the plurality of doctor vectors.

In an example implementation, the doctor vector obtaining unit is configured to update each of the node vectors according to the following equation to obtain the plurality of doctor vectors:

$$h^{t+1}(e_i) = \sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

wherein $W_p$, $W_{ph}$, $W_c$, and $W_{ch}$ are training parameters of the graph neural network, $\sigma$ is an activation function in the graph neural network, t is number of network iterations, $e_i$ is a node corresponding to an i-th doctor in the doctor knowledge graph, $Np(e_i)$ is a parent node set for the node $e_i$, $e_k$ is a k-th parent node of the node $e_i$, $Nc(e_i)$ is a child node set for the node $e_i$, $e_j$ is a j-th child node of the node $e_i$, and $h^t(e_i)$ represents a vector of the node $e_i$ after t network iterations.

In an example implementation, the vector matching module 930 is configured to calculate a matching degree score between the vector of the target outpatient and each of the plurality of doctors according to:

$$score(doc_i, pat_j) = v^T \sigma(W[doc_i, pat_j] + b);$$

wherein $[doc_i, pat_j]$ is a vector obtained by concatenating a i-th doctor vector $doc_i$ and the vector $pat_j$ of the target outpatient, W, v and b are matching parameters, and $\sigma$ is an activation function in the matching degree calculation model.

In an example implementation, the device 900 further includes:

a first model training module configured to train the matching degree calculation model, the graph neural network and the neural network to obtain corresponding matching parameters and neural network parameters; and a data calculation module configured to, based on the matching parameters and the neural network parameters, calculate the matching degree score between the vector of the target outpatient and each of the plurality of doctor vectors.

In an example implementation, the first model training module includes:

a data obtaining unit configured to obtain a training data set, wherein the training data set includes a positive training data set and a negative training data set;

an objective function construction unit configured to input the training data set into the matching degree calculation model, and construct an objective function; and a matching parameter determination unit configured to determine the matching parameters of the matching degree calculation model according to the objective function.

In an example implementation, the matching parameter determination unit is configured to update the matching parameters of the matching degree calculation model using a stochastic gradient descent algorithm, and when the objective function converges, complete the training of the matching parameters.

In an example implementation, the objective function is configured as:

$$L = \sum_{(doc_i, pat_i)} \sum_{(doc_j, pat_i)} [score(doc_j, pat_i) + \gamma - score(doc_i, pat_i)]_+$$

wherein $(doc_i, pat_i)$ is positive training data and represents that an i-th doctor is suitable for dealing with a disease of an i-th patient, $(doc_j, pat_i)$ is negative training data and represents that a j-th doctor is not suitable for dealing with a disease of the i-th patient, $\gamma$ represents a preset difference threshold between a matching degree score $score(doc_i, pat_i)$ of the positive training data and a matching degree score $score(doc_j, pat_i)$ of the negative training data.

In an example implementation, the first model training module is further configured to iteratively update the neural network parameters of the graph neural network by using a backpropagation algorithm, and when an objective function converges, complete the training of the neural network parameters.

In an example implementation, the device 900 further includes:

a to-be-recommended doctor determination module configured to determine a set of doctors to be recommended according to the magnitudes of the matching degrees; and a target doctor recommendation module configured to recommend the doctor for the target outpatient based on the set of doctors to be recommended.

In an example implementation, the target doctor recommendation module includes:

a doctor set recommendation module configured to recommend the set of doctors to be recommended to the target outpatient; and a target doctor determination module configured to, according to a filtering condition input by the target outpatient, performing filtering on each doctor in the set of doctors to be recommended, so as to recommend a target doctor for the target outpatient.

The specific details of each module in the above-mentioned intelligent triage device have been described in detail in the corresponding intelligent triage method, and thus repeated descriptions will be omitted here.

Each module in the above device may be a general-purpose processor, including: a central processing unit, a network processor, and so on; it may also be a digital signal processor, an application-specific integrated circuit, a field programmable gate array or other programmable logic device, discrete gate or transistor logic device, or discrete hardware component. Each module may also be implemented in the form of software, firmware and the like. Each processor in the above device may be an independent processor, or may be integrated together.

It should be noted that although several modules or units of the device for action performance are mentioned in the above detailed descriptions, such division is not mandatory. Indeed, according to embodiments of the present disclosure, the features and functions of two or more modules or units described above may be embodied in one module or unit.

Conversely, the features and functions of one module or unit described above may be further divided into multiple modules or units to be embodied.

It is to be understood that the present disclosure is not limited to the precise structures described above and illustrated in the accompanying drawings, and that various modifications and changes may be made without departing from the scope of the present disclosure. The scope of present disclosure is limited only by the appended claims.

What is claimed is:

1. An intelligent triage method, comprising:

obtaining, by a server, disease information of a target outpatient, and obtaining a vector of the target outpatient according to the disease information;

vectorizing, by a server, each doctor in a doctor knowledge graph to obtain a plurality of doctor vectors, wherein the doctor knowledge graph is constructed by:

selecting Uniform Resource Locators (URLs) as seeds, and putting the URLs into a queue to be crawled;

for seed URLs in the queue to be crawled, accessing website by simulating manual browsing to obtain crawled web Hyper Text Markup Language (HTML) data comprising doctor information;

parsing the doctor information in the crawled web HTML data to obtain a new link, and performing next layer crawling using the new link as a seed URL, to obtain corpus information of a plurality of doctors;

performing, by the server, semantic analysis on the corpus information through natural language processing, and extracting relationships among the plurality of doctors;

with the plurality of doctors as entities, constructing, by the server, the doctor knowledge graph according to the relationships among the plurality of doctors, wherein edges in the doctor knowledge graph represent the relationships between doctors; and calculating, by the server, matching degrees between the vector of the target outpatient and the plurality of doctor vectors using a matching degree calculation model, and recommending a doctor for the target outpatient according to magnitudes of the matching degrees, and sending a recommended doctor to a terminal device of the target outpatient;

wherein vectorizing, by the server, each doctor in the doctor knowledge graph to obtain the plurality of doctor vectors comprises:

vectorizing, by the server, each doctor in the doctor knowledge graph through a graph neural network to obtain the plurality of doctor vectors;

wherein vectorizing, by the server, each doctor in the doctor knowledge graph through the graph neural network to obtain the plurality of doctor vectors comprises:

initializing, by the server, node vectors corresponding to individual doctors in the doctor knowledge graph; and iteratively updating, by the server, each of the node vectors by using a pre-trained graph neural network to obtain the plurality of doctor vectors;

wherein iteratively updating, by the server, each of the node vectors by using the pre-trained graph neural network to obtain the plurality of doctor vectors comprises:

updating, by the server, each of the node vectors according to the following equation to obtain the plurality of doctor vectors:

$$h^{t+1}(e_i) =$$

$$\sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

wherein $W_p$, $W_{ph}$, $W_c$, $W_{ch}$ are parameters of the graph neural network, $\sigma$ is an activation function in the graph neural network, t is number of network iterations, $e_i$ is a node corresponding to an i-th doctor in the doctor knowledge graph, $Np(e_i)$ is a parent node set for the node $e_i$, $e_k$ is a k-th parent node of the node $e_i$, $Nc(e_i)$ is a child node set for the node $e_i$, $e_j$ is a j-th child node of the node $e_i$, and $h^\tau(e_i)$ represents a vector of the node $e_i$ after t network iterations.

2. The intelligent triage method according to claim 1, wherein the disease information comprises text information;

wherein obtaining, by the server, the vector of the target outpatient according to the disease information comprises:

encoding, by the server, each text in the text information to obtain a plurality of phrase vectors; and sequentially inputting, by the server, the plurality of phrase vectors into a pre-trained neural network to obtain the vector of the target outpatient.

3. The intelligent triage method according to claim 1, wherein calculating, by the server, the matching degrees between the vector of the target outpatient and the plurality of doctor vectors using the matching degree calculation model comprises:

calculating, by the server, a matching degree score between the vector of the target outpatient and each of the plurality of doctors according to:

$$score(doc_i, pat_i) = v^T \sigma(W[doc_i, pat_i] + b)$$

wherein $[doc_i, pat_i]$ is a vector obtained by concatenating a i-th doctor vector $doc_i$ and the vector $pat_i$ of the target outpatient, W, v and b are matching parameters, and $\sigma$ is an activation function in the matching degree calculation model.

4. The intelligent triage method according to claim 1, further comprising:

training, by the server, the matching degree calculation model, the graph neural network and the neural network to obtain corresponding matching parameters and neural network parameters; and based on the matching parameters and the neural network parameters, calculating, by the server, the matching degree score between the vector of the target outpatient and each of the plurality of doctor vectors.

5. The intelligent triage method according to claim 4, wherein training, by the server, the matching degree calculation model to obtain the matching parameters of the matching degree calculation model comprises:

obtaining, by the server, a training data set, wherein the training data set comprises a positive training data set and a negative training data set;

inputting, by the server, the training data set into the matching degree calculation model, and constructing an objective function; and determining, by the server, the matching parameters of the matching degree calculation model according to the objective function.

6. The intelligent triage method according to claim 5, wherein determining, by the server, the matching parameters of the matching degree calculation model according to the objective function comprises:

updating, by the server, the matching parameters of the matching degree calculation model using a stochastic gradient descent algorithm, and when the objective function converges, completing the training of the matching parameters.

7. The intelligent triage method according to claim 6, wherein the objective function is:

$$L = \sum_{(doc_i, pat_i)} \sum_{(doc_j, pat_i)} [\text{score}(doc_j, pat_i) + \gamma - \text{score}(doc_i, pat_i)]_+$$

wherein $(doc_i, pat_i)$ is positive training data and represents that an i-th doctor is suitable for dealing with a disease of an i-th patient, $(doc_j, pat_i)$ is negative training data and represents that a j-th doctor is not suitable for dealing with a disease of the i-th patient, $\gamma$ represents a preset difference threshold between a matching degree score $\text{score}(doc_i d, pat_i)$ of the positive training data and a matching degree score $\text{score}(doc_j, pat_i)$ of the negative training data.

8. The intelligent triage method according to claim 4, wherein training, by the server, the graph neural network to obtain neural network parameters of the graph neural network comprises:

iteratively updating, by the server, the neural network parameters of the graph neural network by using a backpropagation algorithm, and when an objective function converges, completing, by the server, the training of the neural network parameters.

9. The intelligent triage method according to claim 1, wherein recommending the doctor for the target outpatient according to magnitudes of the matching degrees comprises:

determining, by the server, a set of doctors to be recommended according to the magnitudes of the matching degrees; and recommending, by the server, the doctor for the target outpatient based on the set of doctors to be recommended.

10. The intelligent triage method according to claim 9, wherein recommending the doctor for the target outpatient based on the set of doctors to be recommended comprises:

recommending, by the server, the set of doctors to be recommended to the target outpatient; and according to a filtering condition input by the target outpatient, performing filtering, by the server, on each doctor in the set of doctors to be recommended, so as to recommend a target doctor for the target outpatient.

11. A server, comprising:

a processor, and a memory storing instructions executable by the processor;

wherein the processor is configured to:

obtain disease information of a target outpatient, and obtaining a vector of the target outpatient according to the disease information;

vectorize each doctor in a doctor knowledge graph to obtain a plurality of doctor vectors, wherein the doctor knowledge graph is constructed by:

selecting Uniform Resource Locators (URLs) as seeds, and putting the URLs into a queue to be crawled;

for the seed URLs in the queue to be crawled, accessing website by simulating manual browsing to obtain crawled web Hyper Text Markup Language (HTML) data comprising doctor information;

parsing the doctor information in the crawled web HTML data to obtain a new link, and performing next layer crawling using the new link as a seed URL, to obtain corpus information of a plurality of doctors;

performing semantic analysis on the corpus information through natural language processing, and extracting relationships among the plurality of doctors;

with the plurality of doctors as entities, constructing the doctor knowledge graph according to the relationships among the plurality of doctors, wherein edges in the doctor knowledge graph represent the relationships between doctors; and calculate matching degrees between the vector of the target outpatient and the plurality of doctor vectors using a matching degree calculation model, and recommend a doctor for the target outpatient according to magnitudes of the matching degrees, and send a recommended doctor to a terminal device of the target outpatient;

wherein the processor is configured to:

vectorize each doctor in the doctor knowledge graph through a graph neural network to obtain the plurality of doctor vectors;

wherein the processor is configured to:

initialize node vectors corresponding to individual doctors in the doctor knowledge graph; and iteratively update each of the node vectors by using a pre-trained graph neural network to obtain the plurality of doctor vectors;

wherein iteratively updating each of the node vectors by using the pre-trained graph neural network to obtain the plurality of doctor vectors comprises:

updating each of the node vectors according to the following equation to obtain the plurality of doctor vectors:

$$h^{t+1}(e_i) =$$

$$\sum_{e_k \in Np(e_i)} \sigma(W_p \times e_i + W_{ph} \times h^t(e_k)) + \sum_{e_j \in Nc(e_i)} \sigma(W_c \times e_i + W_{ch} \times h^t(e_j))$$

wherein $W_p$, $W_{ph}$, $W_c$, and $W_{ch}$ are parameters of the graph neural network, $\sigma$ is an activation function in the graph neural network, t is number of network iterations, $e_i$ is a node corresponding to an i-th doctor in the doctor knowledge graph, $Np(e_i)$ is a parent node set for the node $e_i$, $e_k$, is a k-th parent node of the node $e_i$, $Nc(e_i)$ is a child node set for the node $e_i$, $e_j$ is a j-th child node of the node $e_i$, and $h^\tau(e_i)$ represents a vector of the node $e_i$ after t network iterations.

12. The server according to claim 11, wherein the disease information comprises text information;

wherein the processor is configured to:

encode each text in the text information to obtain a plurality of phrase vectors; and sequentially input the plurality of phrase vectors into a pre-trained neural network to obtain the vector of the target outpatient.

\* \* \* \* \*